(12) United States Patent
Ivansson et al.

(10) Patent No.: US 11,136,598 B2
(45) Date of Patent: Oct. 5, 2021

(54) METHOD FOR CELL LINE DEVELOPMENT

(71) Applicant: Cytiva Sweden AB, Uppsala (SE)

(72) Inventors: Daniel Leif Ivansson, Uppsala (SE); Andreas Castan, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 0 days.

(21) Appl. No.: 15/907,470

(22) Filed: Feb. 28, 2018

(65) Prior Publication Data

US 2018/0251790 A1    Sep. 6, 2018

(30) Foreign Application Priority Data

Mar. 3, 2017 (GB) .................................... 1703417

(51) Int. Cl.
*C12N 15/90* (2006.01)
*C12N 15/11* (2006.01)
*C12N 9/22* (2006.01)

(52) U.S. Cl.
CPC ............ *C12N 15/907* (2013.01); *C12N 9/22* (2013.01); *C12N 15/11* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 5,830,698 A | 11/1998 | Reff et al. |
| 2009/0239305 A1 | 9/2009 | Zhang et al. |

FOREIGN PATENT DOCUMENTS

| EP | 1405908 A1 | 4/2004 |
| EP | 2105505 A1 | 9/2009 |
| WO | 2004/029284 A2 | 4/2004 |
| WO | 2009/130598 A1 | 10/2009 |
| WO | 2014/205192 A2 | 12/2014 |

OTHER PUBLICATIONS

PCT International Search and Written Opinion for PCT Application No. PCT/US2018/032866 dated Jun. 14, 2018 (15 pages).
Kawabe et al., "Repeated Integration of Antibody Genes into a Pre-Selected Chromosomal Locus of CHO Cells Using an Accumulative Site-Specific Gene Integration System," Cytotechnology, 2012, 64:267-269.
Wilke et al., "Streamling Homogenous Glycoprotein Production for Biophysical and Structural Applications by Targeted Cell Line Development," PLoS One, 2011, 6(12):e27829 (8 pages).
Wirth et al., "Road to Precision: Recombinase-Based Targeted Technologies for Genome Engineering," Current Opinion in Biotechnology, 2007, 18:411-419.
GB Combined Search and Examination Report for GB Application No. 1703417.4 dated Dec. 21, 2017 (8 pages).
Bandaranayake et al., "Recent Advances in Mammalian Protein Production," FEBS Lett., 2014, 588(2):253-260.
Campbell et al., "Utilization of Site-Specific Recombination for Generating Therapeutic Protein Producing Cell Lines," Mol. Biotechnol., 2010, 45:199-202.
Jager et al., "High Level Transient Production of Recombinant Antibodies and Antibody Fusion Proteins in HEK293 Cells," BMC Biotechnology, 2013, 13:52 (20 pages).
Schucht et al., "Rapid Establishment of G-Protein-Coupled Receptor-Expressing Cell Lines by Site-Specific Integration," Society for laboratory Automation and Screening, 2011, pp. 323-331.
Zhang et al., "Recombinase-Mediated Cassette Exchange (RMCE) for Monoclonal Antibody Expression in the Commercially Relevant CHOK1SV Cell Line," American Institute of Chemical Engineers, 2015, 31(6):1645-1656.

*Primary Examiner* — Nancy J Leith
(74) *Attorney, Agent, or Firm* — Eversheds Sutherland (US) LLP

(57) ABSTRACT

The present invention relates to an improved method for cell line development which is generally applicable to production of any therapeutic protein that can be produced using mammalian Cell lines and in particular Chinese Hamster Ovary (CHO) cells. The method combines site directed integration (SDI), expression construct components improving the post-transcriptional processing of the gene of interest (GOI), novel design of the GO genome target location and the introduction of a onetime pre-CLD host cell line selection workflow to generate a production competent cell line that can then be used in multiple CLD efforts from that point on.

11 Claims, 6 Drawing Sheets

METHOD FOR CELL LINE DEVELOPMENT

CROSS REFERENCES TO RELATED APPLICATIONS

This application claims the priority benefit of Great Britain Patent Application No. 1703417.4, filed Mar. 3, 2017, the entire contents of which is incorporated herein by reference.

FIELD OF THE INVENTION

The present invention relates to an improved method for cell line development which is generally applicable to production of any therapeutic protein that can be produced using mammalian Cell lines and in particular Chinese Hamster Ovary (CHO) cells.

BACKGROUND OF THE INVENTION

During the latest 30 years recombinant protein therapeutics has evolved from a novelty to a dominating position among marketed drugs. Recombinant production of therapeutic proteins has surpassed the 100 billion $ per year market volume and plays an important role in the global economy as well as in advanced medical care. The therapeutic proteins include replacement proteins (insulin, growth factors, cytokines and blood factors), vaccines (antigens, VLPs) and monoclonal antibodies. The by far dominating format is the monoclonal antibodies. Some of the recombinant proteins can be produced in simple microbial cells such as *E. coli*, but for more complex proteins including the monoclonal antibody class Chinese Hamster Ovary (CHO) cells is the dominating host for production [1]. The monoclonal antibody class is projected to continue being the dominating format but with a larger heterogeneity in molecular structure within this class including different multi-specific formats, fusion proteins, alternative scaffolds and antibody drug conjugates (ADCs). However, since most of these formats will still require advanced protein processing capacity (including glycosylation, disulfide formation and advanced folding machinery) not offered by microbial cells, CHO will likely continue to be the dominating production host for many years to come.

Increased knowledge about the molecular details underlying human diseases has revealed a huge heterogeneity of main diagnoses. As an example, breast cancer is no longer considered to be one disease but consists of at least several 10s of sub-diagnoses. Hence, protein therapeutics is becoming more targeted towards specific molecular mechanisms and will most likely be even more so in the future. Thus an increased number of drugs are needed to enable treatment of whole populations displaying different variants of disease at the molecular level. At the same time there is an increasing pressure to decrease the cost of healthcare, including drugs. Major contributors to the cost of therapeutic protein drugs are the long development time and frequent late failure of drug candidates. One approach to mitigate the risk of late failure and increase the development speed is to evaluate multiple drug candidates early for their developability potential (titer in intended production host, aggregation tendency, formulation stability, immunogenicity). For this to work the production of early protein material must be highly similar to the intended final process and require a minimum of time and effort. For complex protein therapeutics the final production is generally performed in a clonal CHO cell line carrying the recombinant genes stably inserted into the genome by a process referred to as Cell Line Development (CLD).

Currently the mainstream approach to cell line development using e.g. CHO (Chinese hamster ovary) cells is to use random integration of genes of interest followed by (a) selection of cells having the GOI (gene of interest) integrated and (b) a massive screening of clones to find specific clones with favorable production characteristics. The reasons why screening is needed is twofold (i) As a GOI is integrated randomly into the genome the resulting transcription level will be impacted by epigenetic regulation in the region of insertion. A clone having the GOI integrated into one or several highly active and stable genomic locations is needed. Typical cell lines generated generally contain between 5-20 copies of the GOI. (ii) A clone adapted to the burden of expressing a foreign protein at very high levels and with maintained good growth characteristics is needed. However, a CHO host cell is, for example, not a very competent secretor. Further, the CHO genome is highly plastic. By introducing expression of foreign secreted proteins at very high levels an evolutionary pressure towards increased folding and secretory capacity is introduced. By screening many clones, cells better adapted for high secretion can be found. The best random integration platforms today can yield high protein titers in a relatively short time period (~3 months) albeit using a very resource intensive workflow. Further, generated cell clones will be different at the genetic and phenotypic level between different cell line development efforts. This makes early developability assessment to improve efficiency of development difficult and increases process development efforts.

One potentially major improvement is to utilize targeted integration (site-directed integration; SDI) of genes of interest. In such a scenario a pre-identified genomic location known to support high and stable transcription is used as a target destination for GOIs in all CLD efforts. Using intelligent combinations of pre-introduced sequences and vector designs, including the use of co-transfected nucleic acid enzymes such as nucleases or recombinases, will facilitate targeted insertion and ensure that all cells in culture will contain correctly inserted GOIs and hence have a high transcription rate [2-4]. This will significantly reduce the number of clones in the screening campaign. All clones will have the same relatively high transcription rate and hence all clones will also have an evolutionary pressure towards improved handling of the recombinant protein production burden. However, at least two challenges remain (1) SDI generally only integrates a single copy of the GOI and hence the level of expression and evolutionary pressure is generally lower than what can be achieved using random integration and (2) one still need to find a clone that has undergone genetic changes adapting it to e.g. high secretion etc.

SDI ensures a similar level of transcription for both different clones following a specific transfection of a GOI and between different transfections, even using different GOIs. However, numerous changes exist at the genetic and phenotypic level between a typical host cell line lacking recombinant genes in its genome and the final production clone selected during CLD [5]. These differences represent the transformation towards an increased capacity to handle the metabolic burden of producing a foreign recombinant protein at very high levels. Changes will likely include an increased capacity for (i) amino acid synthesis and tRNA charging (ii) protein folding and (iii) protein secretion together with an efficient basic metabolic phenotype. Finding the clone having undergone the desired transformation generally requires substantial screening. The CHO genome is highly plastic and this plasticity forms the engine for introducing variation for screening. However, it is highly likely that the evolutionary pressure of high recombinant protein expression is needed as an inherent selection agent to guide and maintain accumulation of a large number of changes beneficial for recombinant protein production (and avoid accumulation of negative changes) in a single clone.

Thus, to increase speed and enable highly parallel developability assessments, there exists a need of an improved method for cell line development that reduces the need for screening and generates more similar cells between campaigns.

SUMMARY OF THE INVENTION

The present invention provides an improved and novel method for cell line development. The method combines SDI, expression construct components improving the post-transcriptional processing of the GOI, novel design of the GOI genome target location and the introduction of a onetime pre-CLD host cell line selection workflow to generate a production competent cell line that can then be used in multiple CLD efforts from that point on.

In a first aspect, the invention relates to a method for creating a mammalian cell bank for cell line development comprising the following steps:
  (a) providing a recombinant mammalian cell comprising
    (i) a genomic region that is transcriptionally active during suspension culture of said recombinant cell in a serum free culture medium (ii) a recombinant template DNA construct integrated at said genomic region, said recombinant template DNA construct having a region containing elements needed for expression of a template protein of interest and one or several sequence elements enabling the introduction of a donor DNA construct into said template DNA construct;
  (b) based on said recombinant cell or a cell population derived thereof, generating one or several candidate cells or cell populations;
  (c) measuring production traits of said generated candidate cells or cell populations and selecting a top candidate cell or cell population having improved characteristics for production of said template protein of interest; and
  (d) from said top candidate cell or cell population creating a cell bank for cell line development, wherein said donor DNA construct comprises a region encoding a desired protein of interest belonging to the same class as the template protein of interest, and wherein expression of the template protein of interest is exchanged for expression of the desired protein of interest by using an expression vector to introduce said donor DNA construct into said genomic region of a cell or cell population derived from said cell bank.

The same class in respect of protein of interest and template protein refers to a group of proteins sharing a common sequence or structural feature. Examples of protein classes include antibodies of the same class (such as IgG1 antibodies), fusion proteins sharing at least one conserved domain (such as FC-fusion proteins), or in general proteins sharing a conserved scaffold sequence were sequence variation is introduced only at defined region.

Preferably the steps (a) to (c) are iterated in the following way prior to step (d):
  (i) in a next iteration the top candidate cell population from previous step (c) is used as said recombinant mammalian cell in step (a) after having exchanged said template DNA construct for a modified template DNA construct having been modified to provide increased expression potential for said template protein of interest compared to template DNA constructs in earlier iterations; and
  (ii) repeating (a) to (c) n times.

Preferably, the candidate cells or cell populations are generated according to any of the following procedures:
  (a) isolating clones from a culture of said recombinant cell or cell population or descendants thereof; or
  (b) isolating pools or clones after (i) different culture time in a continuous culture format such as a chemostat or (ii) different number of individual cultures starting with inoculation of a first culture using said recombinant cell or cell population or descendants thereof and using a volume from a finished culture to inoculate a next culture or (iii) a combination of (i) and (ii); or
  (c) performing targeted engineering by applying gene editing methods to introduce, remove or modify genetic material in the genome of said recombinant cell or cell population or descendants thereof; or
  (d) using an isolated and expanded clone from a culture of said recombinant cell or cell population or descendants thereof to inoculate a culture in procedure (b) or
  (e) any combination of procedure (a) to (d).

The template protein of interest may be coded by a single gene of interest, such as growth factors, blood clotting factors, cytokines, hormones, erythropoietins, albumins, virus proteins, virus protein mimics, bacterial proteins, bacterial protein mimics, domain antibodies, ScFvs, Affibodies, DARPINs, multimerization domains, IgG Fc domains, albumin binding domains, Fc receptor binding domains or fusion proteins based on combinations of the above single gene of interest coded protein classes. Alternatively, the template protein of interest is coded by two or more genes of interest such as monoclonal antibodies based on naturally occurring scaffolds, bi-specific antibodies based on naturally occurring scaffolds, Fabs, virus like particles, multiple chain proteins based on association of two or more different protein chains selected.

In a second aspect, the invention relates to a method for mammalian cell line development comprising the following steps:
  (a) providing a cell or cell population from a mammalian cell bank developed according as above and (i) having a final template DNA construct with a template protein of interest coding region including promoter(s), a first selection marker coding region including promoter(s) and a sequence z being unique or rare in the total genome sequence of said cell or cell population and wherein said coding regions and said sequence z can be in any order (ii) said final template DNA construct being flanked by two sequence stretches X and Y being unique or rare in the genome of said cell;
  (b) providing a matching expression vector in the form of a plasmid containing sequence stretches X' and Y' being homologous to said sequence stretches X and Y and wherein said sequences X' and Y' flanks a desired protein of interest coding region including promoter(s) and a second selection marker coding region including promoter(s);

(c) introducing vector(s) coding for a gene editing nuclease with specificity for sequence z together with said expression vector into said cell or cell population and wherein said gene editing nuclease is designed using any available technology platform such as zinc finger nucleases, meganucleases, TALENs or CRISPR/Cas9 designs;
(d) said genome editing nuclease generates a double strand break at sequence z catalyzing exchange of the regions flanked by said sequences X and Y in said template DNA construct and sequences X' and Y' in said expression vector via cellular DNA repair mechanisms;
(e) a cell or cells having undergone correct cassette exchange only are selected via the use of selection marker(s) and/or genetic characterization.

Alternatively the second aspect comprises a method for mammalian cell line development comprising the following steps:
(a) providing a cell or cell population from a mammalian cell bank developed as above and having a final template DNA construct with two recombinase recognition sequences flanking a template protein of interest coding region and a first selection marker coding region in any order and orientation and wherein promoters for said coding regions can either be flanked by or be located outside of said recombinase recognition sequences and wherein said recombinase recognition sequences are both of the same type such as a serine recombinase type such as attP/attB or a tyrosine recombinase type such as Lox, Rox or FRT;
(b) providing a matching expression vector in the form of a plasmid containing two recombinase recognition sequences flanking a desired protein of interest coding region and a second selection marker coding region, and wherein said recombinase recognition sequences in the expression vector are of the same type as and matching said recombinase recognition sequences in said template DNA construct;
(c) introducing said expression vector together with vector(s) coding for a recombinase, and wherein said recombinase is of any type matching said recombinase recognition sequences in said template DNA construct and said expression vector such as one selected from the group of PhiC31, Cre, Dre, or Flp;
(d) said recombinase catalyzes the exchange of the regions flanked by said recognition sequences in said final template DNA construct and said expression vector;
(e) a cell or cells having undergone correct cassette exchange only are selected via the use of selection marker(s) and/or genetic characterization.

According to a further embodiment the method for mammalian cell line development comprising the following steps:
(a) providing a cell or cell population from a mammalian cell bank developed as above and having a final template DNA construct with a single recombinase recognition sequence followed by a template protein of interest coding region and a first selection marker coding region in any order and orientation and wherein promoters for said coding regions can be located either 5' or 3' of said recombinase recognition sequence and wherein said recombinase recognition sequence is of a type such as serine recombinase type such as attP/attB or a tyrosine recombinase type such as Lox, Rox or FRT;
(b) providing a matching expression vector in the form of a plasmid containing a recombinase recognition sequence followed by a desired protein of interest coding region and a second selection marker coding region, and wherein said recombinase recognition sequence in the expression vector is of the same type as and matching said recombinase recognition sequence in said template DNA construct;
(c) introducing said expression vector together with vector(s) coding for a recombinase, and wherein said recombinase is of any type matching said recombinase recognition sequences in said template DNA construct and said expression vector such as one selected from the group of PhiC31, Cre, Dre, or Flp;
(d) said recombinase catalyzes the integration of said expression vector at said recognition sequence in said final template DNA construct resulting in the presence of a functional region for expression of said desired protein of interest and a region for said template protein of interest that either lack a promoter or contain an inducible promoter enabling shut down of expression activity for said template protein of interest using conditions with maintained expression activity for said desired protein of interest;
(e) a cell or cells having undergone correct integration of the expression vector only are selected via the use of selection marker(s) and/or genetic characterization.

In these three latter methods the template protein of interest and said desired protein of interest are identical at the amino acid sequence level.

In all embodiments of the invention the mammalian host cell line is preferably a CHO cell line such as CHO DG44, CHO K1, CHO M, CHO-S or a CHO GS knockout cell line.

DETAILED DESCRIPTION OF THE INVENTION

Figure 1A:
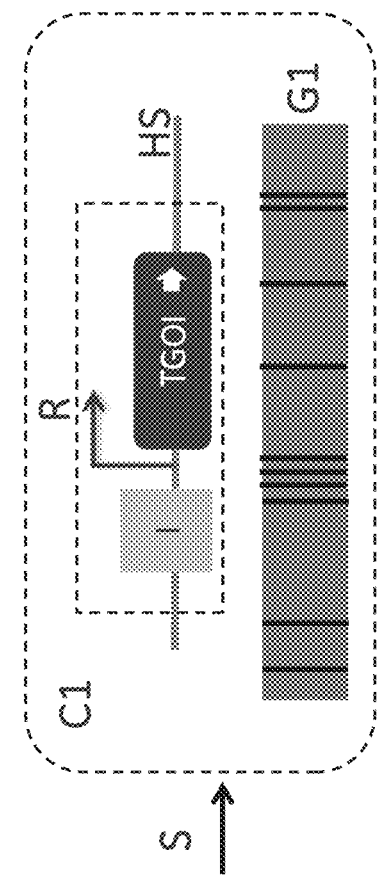
FIG. 1a is a schematic view of a conceptual general workflow for generating a host cell with improved properties.
Figure 1A:
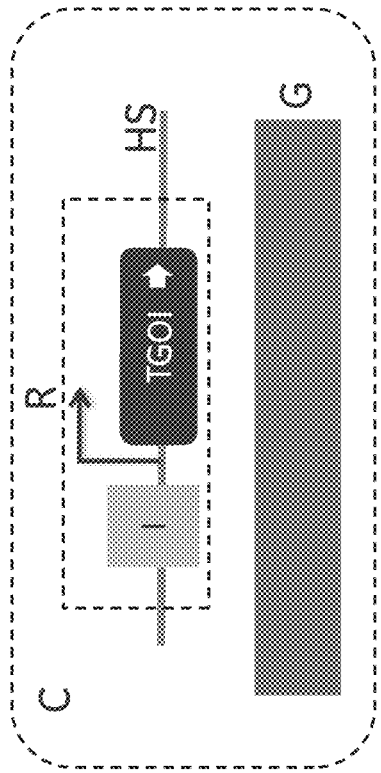

The invention will now be described more closely in association with the accompanying drawings and some non-limiting Examples.

The key component for the different embodiments of the invention is the presence of a single copy of template gene(s) of interest (TGOI) coding for a template protein of interest at a defined genomic location (transcriptional hot spot or HS) in the intended host cell line to be used for Cell Line Development (CLD). Further, the presence of nucleic acid sequences that enables a workflow for disabling the TGOI and introducing desired gene(s) of interest (GOI) coding for a desired protein of interest, preferably of the same protein class, at the same genomic location (HS) so that there is always one active and highly expressed recombinant GOI during all handling of cells in the CLD workflow. The reason why this is critical is that the presence of a TGOI introduces a defined expression challenge and a recombinant expression load on the cell that enables utilizing the genomic instability of typical host cell lines such as Chinese Hamster Ovary cells (CHO cells) to generate improved production phenotypes and hence frontload the screening/selection work needed to isolate a cell clone that can produce a certain class of recombinant protein at a high level and with proper quality. Further, the continuous presence of this recombinant expression load at a defined and similar level ensures that positive changes are not lost during culture due to genetic instability before introduction of the GOI. The GOI codes for a recombinant desired protein of interest sought to be produced in significant amounts and the TGOI codes for a recombinant template protein of interest with similar properties as the protein of interest. The template protein of interest and the desired protein of interest are of the same protein class, such as for example monoclonal antibodies of the IgG1 subtype, and their constructs contain identical expression elements such as promoters, 5'-UTRs, 3'-UTRs and signal peptides.

A typical limitation of SDI based CLD approaches utilizing a single copy of the GOI known in the art have been to reach high enough total protein translation rates. A typical cell line generated using random integration typically contains 5-20 copies of the GOI and hence gives a higher total protein translation rate based on higher mRNA levels. The single copy integration limits the maximum cell specific productivity obtainable using a specific recombinant gene construct design, but is also likely to negatively impact the selection of a high productivity phenotype as a lower expression load limits the detection of high performing phenotypes in a heterogenic population as the best phenotypes capable of expressing the protein well above the expression load cannot be distinguished from medium performance phenotypes just coping with the expression load. Hence, an important feature of the invention is to ensure a recombinant gene construct design enabling highly efficient mRNA translation to compensate for the lower mRNA levels or to use alternative promoters enabling increased mRNA levels from a single gene copy. In some embodiments this can be achieved by sequence designs promoting increased ribosome recruitment, increased translation initiation and optimized speed and minimized error rates in the translation elongation of the coding region. In a preferred embodiment of the method of the invention use is made of translational enhancement elements (TEEs) [6] in the 5'-UTR and RESCUE modification [7] of the coding region.

With the combined solution described above, utilizing a high performance host cell line pre-selected via the aid of a TGOI and optimized gene constructs, competitive titers using single copy GOI integration will be possible and since screening of clones is expected to be at a minimum the time and resources needed for a CLD campaign will be significantly reduced allowing cost savings by shortened time to clinic and market. Since cells generated from different CLD efforts using different candidate constructs are expected to be highly similar both at the genetic and phenotypic level it will be possible to perform comparisons of developability traits (immunogenicity, protein titers, aggregation levels, protein self-association, binding specificity, formulation stability etc.) for an increased number of protein candidates in each drug development program and with stable cell lines identical to ones used in final production and without the data being corrupted by variation coming from differences in the physiological state of cell lines. This can in turn enable even larger cost savings and efficiency increases in drug development by increasing the likelihood of success and reducing the rates of late failures. In addition, by having control of the gene copy number as well as other expression elements of the GOIs and having increased control over the expression stability of GOIs more ambitious and pro-longed screening of host cell clonal diversity can be performed with potential to generate phenotypes with superior production traits for a certain protein class as compared to typical cell lines generated using random integration approaches or SDI approaches with modest screening known in the art. Finally an improved host cell line generated using any of the embodiments of the invention, can be used for any desired number of CLD efforts using different desired proteins of interest of a similar protein class.

Figure 1B:
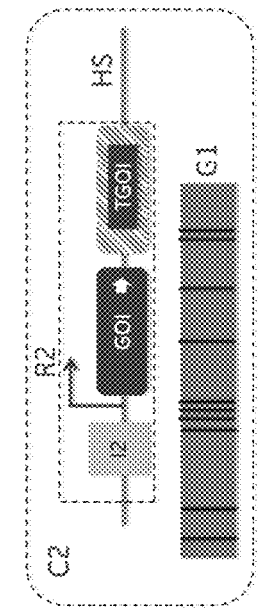
FIG. 1b describes the use of the improved host cell C1 in a streamlined CLD workflow based on targeted integration.
Figure 1B:
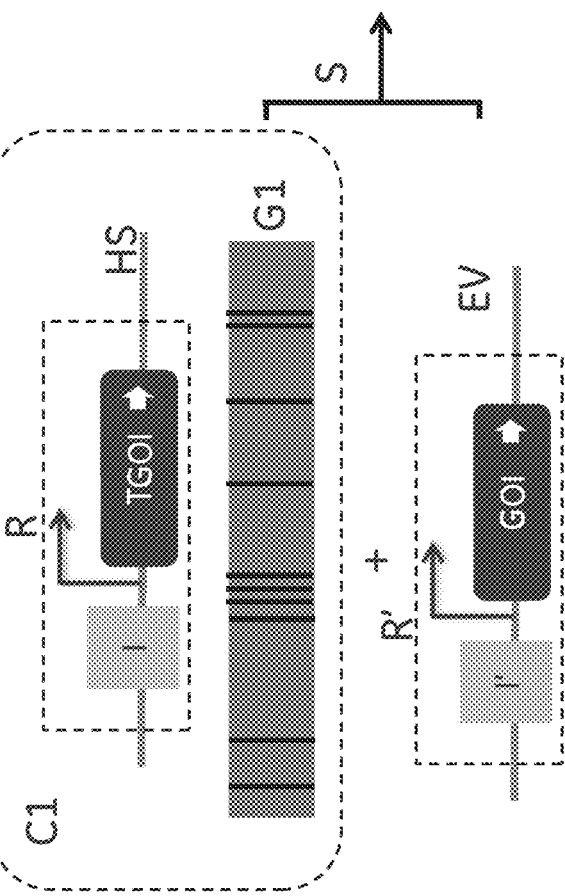

A conceptual general workflow for generating such a host cell line with improved properties can be found in FIG. 1a. First, an initial mammalian cell (C) carrying a single copy of a template DNA construct (R) at a defined location in the genome (HS) is provided. This cell is then put through a selection workflow (S) to isolate/select a cell (C1) with highly increased capacity to produce the template protein of interest. The improved C1 cell will have a modified genome (G1) and/or transcriptome compared to the original cell genome (G1) and/or transcriptome reflecting multiple accumulated changes in diverse cellular pathways and processes which together give rise to a phenotype with the improved expression capacity. The improved cell C1 can then be used in a streamlined CLD workflow (FIG. 1b) in which C1 is contacted with an expression vector (EV) containing a matching recombinant construct R' enabling a switch in expression from the template protein of interest to a desired protein of interest by introduction of R' from EV to create a cell C2 maintaining the expression phenotype and genome (G1) of C1 but now expressing the desired protein of interest. The genomic location should preferably be a hot spot region, meaning that it supports high transcription of introduced genes and that this transcription is stable over time and reproducible for different genes and different culture conditions. Especially the transcription activity should be high and stable using a serum free culture medium and growth during suspension conditions. Hot spot regions can be identified either via screening approaches, bioinformatics or a combination of these. The current invention builds on that a defined genomic location has been selected and that the sequence of this genomic site is known. The template DNA construct (R) contains a TGOI and optionally gene(s) coding for selection marker(s) (SM(s)). Preferably the TGOI design contains genetic elements either outside or inside the coding sequence(s) providing a high level translation power for the corresponding protein to maximize the expression load/potential. Such elements can include strong promoters such as mCMV, hCMV or synthetic promoters [13], 5'-UTR designs providing increased mRNA stability and/or increased translation, 3'-UTR designs providing increased mRNA stability and/or increased translation, signal peptides providing improved secretion properties and optimized sequence stretches in coding regions based on synonymous codon changes. Preferentially, design of these sequence elements are based on TEEs in the 5'-UTR and RESCUE-modification of the coding region [6, 7].

The template DNA construct R further contain one or several sequences I and the expression vector EV one or several sequences I' that together enables the simultaneous inactivation of TGOI expression and introduction of an alternative recombinant DNA construct R' as C1 is contacted with EV. Introduction of R' results in the creation of a new recombinant construct R2 being present in C2, carrying a GOI, one or several sequences 12 generated from I and I' and optionally a second set of SM(s). The new recombinant DNA construct R2 can be of two main categories. R2 is either (1) created by a cassette exchange between R and R' leading to the absence of TGOI and the optional first set of SM(s) in R2 or (2) by addition of R' to R so that the TGOI is still present in R2 but no longer active due lack of proximity to a promoter or due to a change in culture conditions switching off TGOI promoter(s) while keeping GOI promoter(s) active. Specific implementations will be further described later.

Figure 2:
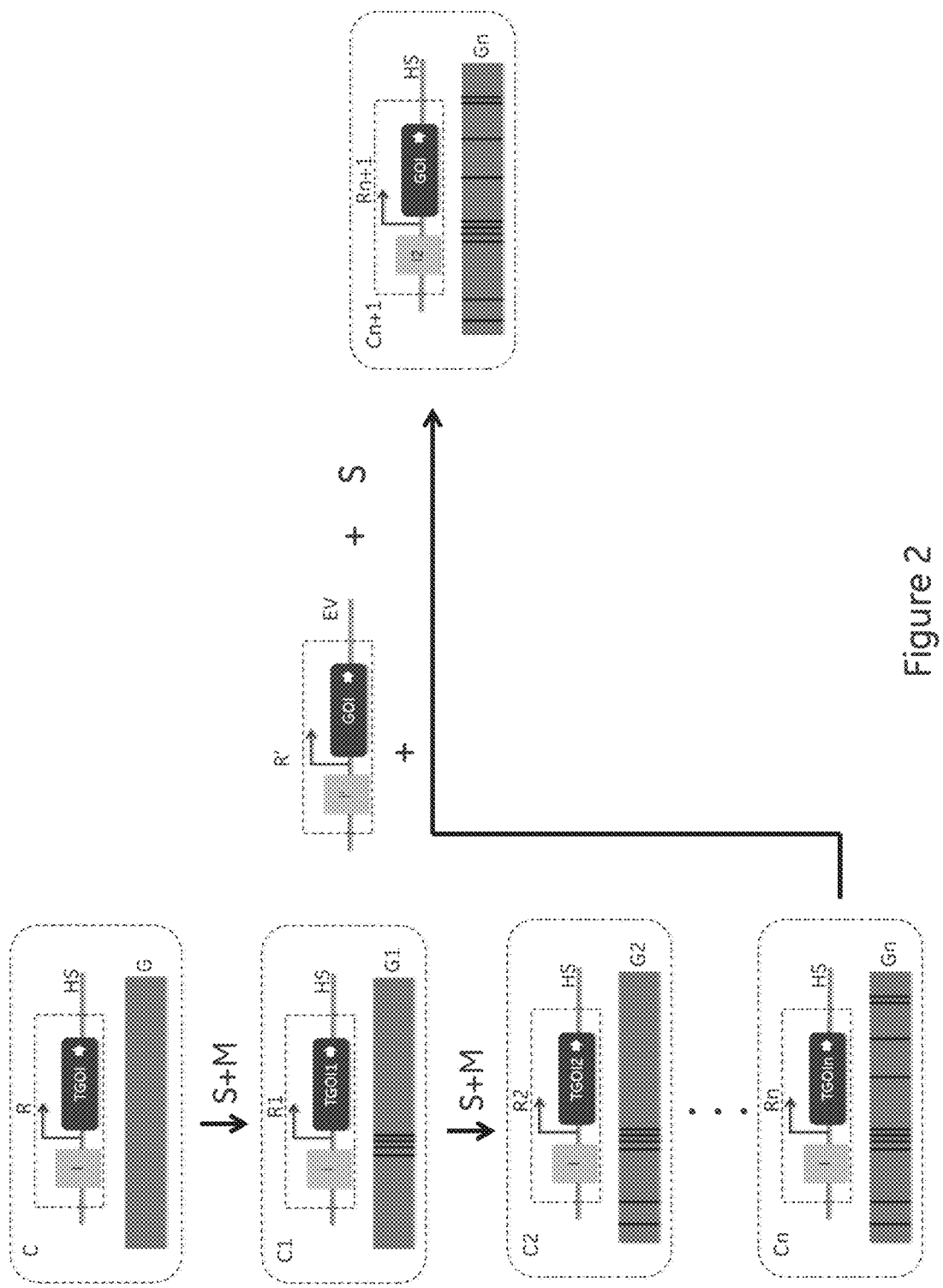
FIG. 2 is a schematic view of an alternative way of generating an improved host cell using an iterative approach in which different TGOI constructs all coding for the same protein but providing different expression loads are introduced during each new iteration in a way so that the expression load is gradually increased following isolation of a top cell candidate at the previous expression load.
Figure 3:
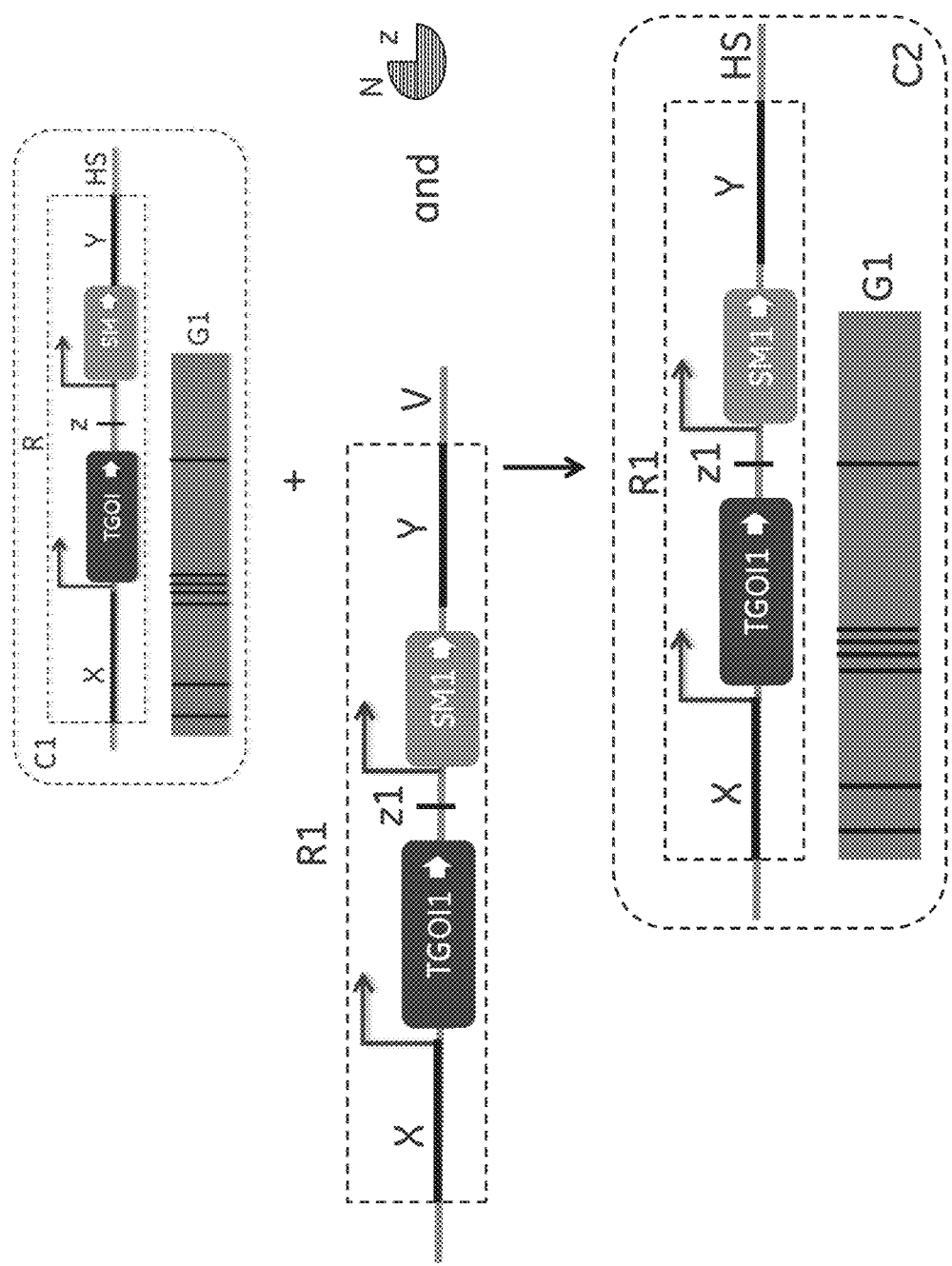
FIG. 3 describes a further embodiment of the iterative approach in FIG. 2 based on the use of Double Strand Break induced homologous recombination for exchange of TGOI variants.

The generation of an improved cell can either be performed using a single TGOI expression load as outlined in FIG. 1 or by an iterative improvement workflow in which the expression load is gradually increased and intermittent improved cells are isolated after each increase in expression load until a final improved cell is generated as outlined in FIG. 2. In this workflow the first step improved cell carrying a recombinant DNA construct R enabling a first TGOI expression load is contacted with exchange vector(s) enabling removal of R and introduction of a new template DNA construct R1 enabling a second higher TGOI expression load. This in turn enables the selection of a second step improved cell. This gradual increase in expression load can be repeated any number of times until a final improved cell is generated. The expression load can be varied by using different promoter strengths in different TGOI construct generations, by utilizing 5'-UTR and 3'-UTR variants promoting different mRNA stability and/or translational efficiency, by utilizing coding sequences promoting different mRNA stability and/or translational efficiency or by changing the TGOI copy number between different generations. One specific embodiment of this iterative approach is to utilize cassette exchange mediated by a double stand break inducing site specific nuclease as outlined in FIG. 3. Here the template DNA construct R contains a sequence X at the 5'-end, a sequence Y at the 3'-end and an internal sequence z. All sequences X, Y and z are unique or rare in the genome (G1) of cell C1. To exchange R for R1 the cell C1 is contacted with an exchange vector V carrying R1 and a site specific nuclease with specificity for z. R1 contain sequences at the ends that are either identical to or highly similar to the sequences X and Y in R. The site specific nuclease creates a double strand break at z catalyzing cassette exchange between R and R1 via homologous recombination repair mechanisms using R1 as a repair template. If additional cassette exchange reactions are planned R1 should also contain a sequence z1 being unique or rare in the genome (G1) to enable cassette exchange using a second site specific nuclease with specificity for z1. The site specific nuclease can be any type of gene editing solution such as zinc finger nucleases, homing endonucleases, TALENs or CRISPR/Cas9 variants. An alternative to using gene editing assisted homologous recombination for exchanging TGOI variants is to utilize reversible recombinase systems such as solutions based on Cre/loxP in which a first TGOI variant can be introduced at a loxP sequence via the aid of the Cre recombinase resulting in an introduced TGOI flanked by two loxP sequences. Following isolation of an improved cell the first generation TGOI can be removed via the action of Cre which re-creates the single loxP sequence enabling introduction of a second generation TGOI.

Two main approaches can be used to isolate an improved cell from an initial TGOI carrying cell. The first approach utilizes the inherent plasticity of the genome of typical mammalian host cell lines used for recombinant protein production. One embodiment of this approach to generate an improved cell line with improved properties is to screen clones from a culture for a desired set of protein production traits and select the top performing clone. Protein production traits could be, but are not limited to: template protein of interest production rate or culture titer, template protein of interest aggregation level, template protein of interest charge heterogeneity, template protein of interest size heterogeneity, glycosylation site occupancy and glycosylation profile for the template protein of interest, cell growth characteristics and cell metabolic characteristics, tertiary structure profile for the template protein of interest, template protein of interest self-association tendency, DNA sequence profiles, mRNA profiles, miRNA profiles, proteomic profiles and genomic stability of cells. This can in principle be performed in analogy with current CLD screening approaches used in the field. There initial screens of many clones using simple parallel culture formats and a few measured parameters such as titer and growth are followed by more extensive screening, including protein quality attributes as described above, of a lower amount of selected clones in more predictive culture formats such as shake flasks or bioreactors.

A second embodiment is based on directed evolution of the cells via pro-longed culture of the cells with recombinant expression pressure present. The high recombinant expression load imposed on all cells will have an impact on the viability and growth. Cells that do not handle the recombinant expression load well are hypothesized to be subjected to stress responses (amino acid shortage, charged tRNA shortage, hold up of the ribosomal machinery of recombinant mRNAs, hold up of the folding machinery on recombinant proteins, build-up of soluble or aggregated forms of recombinant protein within cells) reducing viability and growth. Further, cells having genetic/epigenetic changes leading to an improved handling of the recombinant expression load are hypothesized to have a higher viability and growth. Hence, by culturing cells for many generations, far exceeding what is used in typical CLD workflows, a large diversity of genetic/epigenetic changes are sampled and enrichment of cells having accumulated multiple positive changes are hypothesized based on this directed evolution mechanism.

Preferentially the TGOI codes for a template protein of interest representing an important class of proteins such as IgG1 antibodies or FC-fusion proteins and preferentially a difficult to express protein of this class to promote isolation of the highest possible production competency of the generated host cell line. Preferentially the culture of the cells is performed using conditions highly similar to a platform process defined for production of protein for clinical phases or commercial purposes to enable the adaptation through directed evolution to be directly compatible with these conditions. This could for example mean using a bioreactor fed-batch culture with defined culture medium, feed medium and process parameters. Pro-longed culture in this format could for example be achieved by inoculation of next generation cultures using a fraction of the culture from the previous culture. Prolonged culture could also be achieved in a chemostat reactor or a perfusion culture, potentially repeated multiple times using seeding of cells from a previous culture stage. Preferentially a selection marker, such as Neomycin resistance, a DHFR gene or a GS gene, is used together with culture conditions that put a strong selection pressure for the presence of an active selection marker. This could for example be the use of a neomycin resistance gene as selection marker and the use of neomycin during culture.

Another potential selection marker design could utilize a genetic circuit coupling cellular survival directly to expression of the TGOI. Such a genetic circuit could be based on non-native miRNAs binding both to a sequence stretch of TGOI mRNA and a sequence stretch on a selection marker gene such as NeoR, GS or DHFR. This is to further ensure, in addition to the use of a transcription hot spot region, that the expression construct is not silenced during culture leading to the enrichment of cells that are not expressing the template protein of interest. This approach has the potential to generate superior protein production clones as compared to approaches based on mere screening of clones. Typically in screening approaches a first culture is performed to select a first set of clones from. Individual clones are cultured for assessment followed by a second selection of clones. This is repeated a few times. As genetic variants are removed early and a low number of generations are allowed between selection steps a relatively low amount of genome variation is sampled using this approach. Using directed evolution and pro-longed culture for many generations keep all the genetic variation and allows time for accumulation of rare modifications and most importantly rare combinations of changes. Importantly, using this approach on a cell line lacking a TGOI would most certainly not lead to the same accumulation of positive protein production traits as most such changes would not be favored without the evolutionary pressure of high recombinant expression load and would not be possible to detect without the presence of a TGOI. Directed evolution and screening can also be combined and preferentially at least one final step including screening of production traits should be included. Intermediate screening steps in a workflow based on directed evolution can be used to further ensure that the rare event of clones having managed to silence the SM/TGOI does not lead to such cells being enriched in cultures. Finally, a clone or a pool of cells isolated from any of these workflows is used to create a master cell bank (MSB) of a final improved host cell line. The final host cell line having accumulated genetic and/or epigenetic changes compared to the initial host cell line and recombinant mammalian host cell. In addition to the phenotypic diversity generated during cell growth, phenotypic diversity could also be artificially increased between selection/screening rounds by use of chemicals such as epigenetic de-regulators or by radiation increasing mutation rates.

Besides utilizing the natural or artificially enhanced plasticity in the genome to sample random changes, a second approach based on targeted engineering can also be used to generate the final host cell line for CLD. A cell (C) according to FIG. 1a being subjected to a defined TGOI expression load is subjected to targeted changes to the genome (G) via the use of genome editing enzymes (Zinc finger nucleases, meganucleases, TALENs, CRISPR/Cas9 variants) and recombinant nucleic acid donor constructs to knock-out genetic functionality or add novel genetic functionality. After selection of cells having undergone correct/desired changes, the effect of these targeted changes is evaluated in follow up cultures to look at protein production traits such as those described above.

A range of different individual targeted changes can be evaluated and cells with targeted changes having positive effects on protein production traits can then be subjected to an iterative approach adding and evaluating additional changes. This process can be repeated until a final clone or cell pool with desired properties (based on the accumulation of one or multiple targeted changes) can be isolated. Preferentially the evaluation of protein production traits is performed using culture conditions highly similar to a platform process defined for production of proteins for clinical phases or commercial purposes to enable a fit to these conditions. This could for example mean using a bioreactor fed-batch culture with defined culture medium, feed medium and process parameters. Compared to targeted engineering approaches applied on host cell lines lacking a TGOI, the method according to the present invention enables several major advantages. First, the presence of a TGOI with controlled expression properties that can be reproduced for any GOI of the same class following CLD enables evaluation of targeted changes to be performed in conditions that are predictive of the intended final use. Secondly, the continuous presence of an expression load during the engineering workflow and subsequent culturing during CLD reduces the risk of loss of functionality due to genetic instability. As an added feature directed evolution, screening of natural genetic diversity and targeted changes can be combined in any form together with conditions predictable to the final use to generate the final improved host cell line. In one embodiment of the invention the instability of the host cell genome is first used to enable generation of an improved host cell via multiple genetic and/or epigenetic changes throughout the genome that would likely be difficult to generate using targeted engineering alone. In a second stage the instability of the genome is reduced either via directed evolution/selection or via targeted engineering. Research is currently underway to define engineering targets enabling stabilization of the genome of for example CHO cells [8].

As previously described the isolation/selection steps can also be repeated multiple times using a gradually increased expression load as outlined in FIG. 2. The rationale for a stepwise increase in the expression load is to enable a gradual move towards a higher performance phenotype. If the initial expression load is too high a low number of clones will be capable of matching this expression load and show up as competent producers during screening and hence a low number of clones can be passed on to a second round of growth and screening. This leads to an early potentially detrimental reduction of phenotypic diversity. There is a high risk for a low survival frequency and very low growth of cultured cells again leading to an inefficient sampling of clonal variation and slow accumulation of improved phenotypes. The initial clonal variation might not even be sufficient to enable survival of any cells at all. By gradually increasing the expression load cells can gradually adapt and an increased genetic variation can be sampled and taken forward in each iteration.

The use of a host cell line based on an improved cell generated using any of the above workflows together with expression vectors for Site-Directed Integration (SDI) enables a highly streamlined CLD workflow. Current methods known in the art are generally based on either random integration of expression constructs or targeted integration of expression constructs into a genomic location having a SM region only. Using the random integration approach a pool of cells that are all actively transcribing genes in the expression construct can be generated via the aid of a selection marker. However, different clones will have the expression construct integrated at different genomic locations and with different number of copies. This in turn will result in a range of transcription levels and importantly different clones will also display varying stability of transcription over time and during different culture conditions. In addition different clones will display different protein production traits. In summary this leads to a need of massive screening efforts to isolate a clone with both good transcription levels and good protein production traits.

Furthermore, repeating the CLD using either an identical expression construct or a variant expression construct will lead to cells that are different at the genetic and phenotypic level making it difficult to evaluate optimal expression construct and GOI designs. Using a targeted approach simplifies the workflow by the introduction of a single copy of the expression construct into a pre-defined/pre-characterized genomic location. The delivery of the expression construct to the defined location is aided by the presence of specific sequences at the genomic location and in the expression constructs and via the co-transfection of a vector coding for a nucleic acid enzyme. The enzyme can either be a nuclease introducing a double strand break unique to the genomic location and integration proceeds via homologous recombination between a long stretch of homologous sequences present at the genomic site and in the expression construct. As an alternative, shorter specific nucleotide sequences acting as target sequences for recombinases can be present at the genomic location and in the expression construct. The co-transfected recombinase will then catalyze the integration of the expression construct. After utilizing selection via a second SM set a pool of cells all carrying a single copy of the expression construct and displaying similar transcription levels can be generated. However, different clones will still display different protein production traits and hence there is a need for a clone screening procedure to isolate a cell with the desired traits. Although the screening should be reduced as compared to random integration it could still be a significant effort and cells can still be different between different CLD efforts.

However, using the host cell line and the CLD methodology of the present invention potentially removes both of the above sources for variation and screening need and can potentially generate production clones/pools with superior production traits as compared to current screening based methods. An improved host cell generated according to any combination of the approaches described above already displays the desired protein production traits and has a template DNA construct with a TGOI and optionally a first set of selection marker(s) integrated at the desired genomic location. Further, this template DNA construct contains sequence(s) that enables the simultaneous inactivation of the TGOI and the integration of a region from an expression vector carrying a GOI and an optional second selection marker region. As described in more detail later this can be achieved in different ways depending on the design of the template DNA constructs and matching expression vectors. After selecting for proper exchange or inactivation/integration using a combination of the first and second selection marker sets a pool of cells with limited diversity is generated. In principle, a clone from this pool could be isolated without further screening and only characterized to ensure that a single correct cassette exchange has occurred and no additional random integration.

Some examples of improvements over standard workflows have been described in previous art. First, directed evolution of a final host cell line has been proposed [9]. However, in this case directed evolution is performed on an initial cell line lacking the introduction of recombinant genes or a hot spot integration site and selection traits are not directly linked to protein production traits. Further, the generated host cell line is then utilizing random integration for CLD. Host cells generated using this approach will not have been subjected to a pressure to accumulate changes improving protein production traits and as adaptation to specific culture conditions has been done without the recombinant expression burden there is a risk for sub-optimal adaptation to the conditions experienced during production of a recombinant protein.

The present invention represents several improvements over this approach. The presence of the TGOI enables selection/evolution of protein production traits matching the combined demands of the specific culture conditions and a high level recombinant expression pressure. Further, the continuous presence of the TGOI reduces the risk for loss of adaptation due to genetic instability. Finally, the cassette exchange approach to CLD enables the conditions experienced by the cells following introduction of the GOI (at the same location, with the same copy number and with the same sequence elements) to be highly similar to the conditions used during generation of the host cell line. Utilization of pre-adapted cells has also been proposed for targeted integration based CLD [10]. In this approach it is proposed that a cell line generated using random integration CLD and displaying desired protein production traits should be selected as a source for generating a final host cell line. In the proposed procedure, the genomic location is identified (must be a single site) and the recombinant constructs are cut out using gene editing based homologous recombination and exchanged for a construct carrying a selection marker flanked by recombinase sequences.

After isolation of cells having undergone correct exchange, the genomic site is treated with a recombinase to cut out the selection marker and leave a single recombinase site flanked by a promoter. This host cell line can then be used for targeted integration of a second expression construct. In this approach there is not a match between the expression load provided by the multiple copies of the first expression construct and the single copy of a second expression construct following CLD. Hence, the properties of the host cell line are not likely to be fully suitable to the new conditions. This mismatch can be further increased if the culture conditions are different between the initial cell line and the second cell line. In addition, after the exchange of the original expression construct there are multiple culture periods during both the construction of the host cell line and each CLD effort where the lack of recombinant expression load can lead to loss of accumulated traits and increased diversity of cells due to genetic instability. Hence, the current invention offers multiple improvements over this approach in that the selection/evolution of traits can be better matched between host cell line and the cell line producing the GOI after CLD. In addition the presence of the TGOI or the GOI at a similar expression load throughout all culture steps minimize the risk of loss of functionality/ increased cell diversity due to genetic instability. In addition the increased sampling of diversity possible by directed evolution and the possibility to add targeted modifications has the potential to generate production clones with superior protein production traits.

Using the natural diversity of cells has recently been discussed and highlighted as a potentially superior approach in a GEN article [13]. Using selection to generate a high performance cell expressing a certain template protein is here contemplated. However instead of isolating this cell and using it directly in subsequent CLD workflows the potential to identify engineering targets by detailed omics characterization to enable reproduction of a high productivity cellular phenotype using targeting engineering approaches is proposed.

Figure 4:
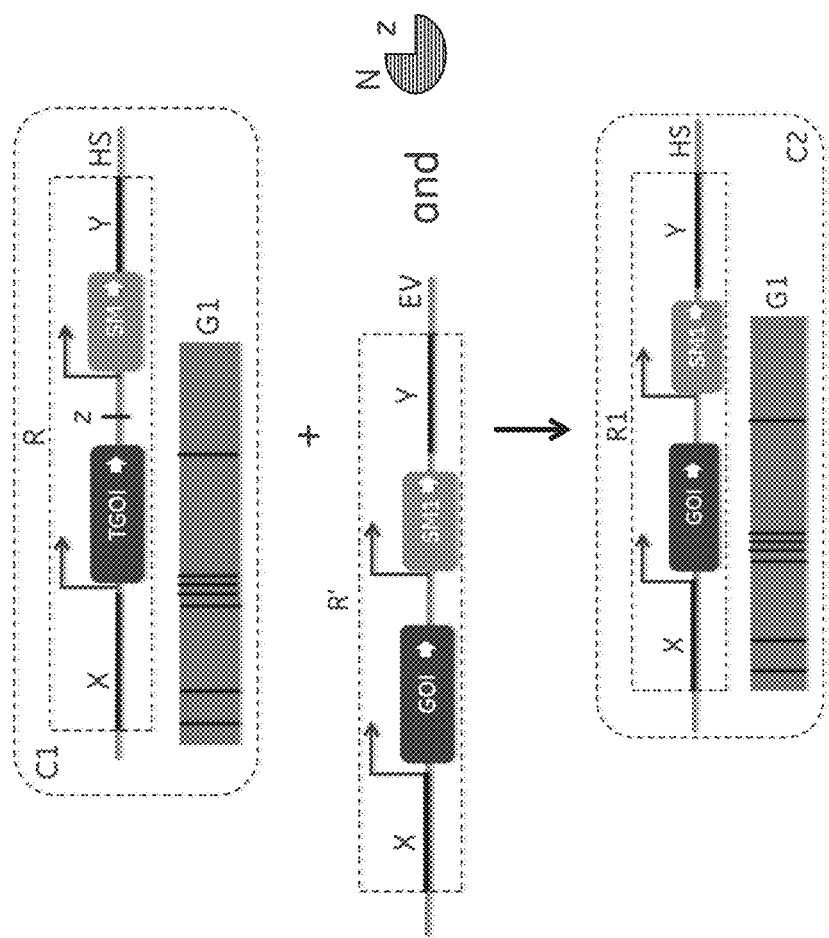
FIG. 4 describes a specific embodiment for CLD using an improved cell C1 of the FIG. 1 method using cassette exchange based on the use of Double Strand Break induced homologous recombination for exchanging a TGOI for a desired GOI.

Following the detailed outline of the general concept of the invention above specific implementations will now be described. In a first specific implementation the template DNA construct R and the expression vector EV is designed as outlined in FIG. 4. Here R contains a TGOI gene(s) with accompanying promoter(s) and a selection marker gene(s) with accompanying promoter (s). Flanking these genes are a sequence X at the 5'-end and a sequence Y at the 3'-end and the construct further contain an internal sequence z. Sequences X, Y and z are all unique or rare in the genome (G1) of the improved cell C1. Further X and Y are long sequences above 200 bp and typically in the range of 1 Kb whereas z is shorter, typically in the range of 15-40 bp. The matching expression vector EV contain a GOI(s) with accompanying promoter(s) and a second selection marker(s) with accompanying promoter(s) both being flanked by two sequences at the ends being either identical or highly homologous to sequences X and Y. By contacting the improved cell C1 with the expression vector EV and a site specific nuclease with specificity for z cassette exchange between R and R' is achieved via double strand break induced homologous recombination mediated via the homologous sequence stretches in R and R'. The difference in selection markers between R and R' can be used to isolate cells having undergone the correct cassette exchange only. The site specific nuclease can be based on any gene editing solution such as zinc finger nucleases, homing endonucleases, TALENs or CRISPR/Cas9 variants. The expression vector is typically provided in the form of a plasmid and is typically introduced into cells together with a plasmid encoding the selected site specific nuclease using any transfection methodology known in the art, such as lipofection or electroporation.

Figure 5:
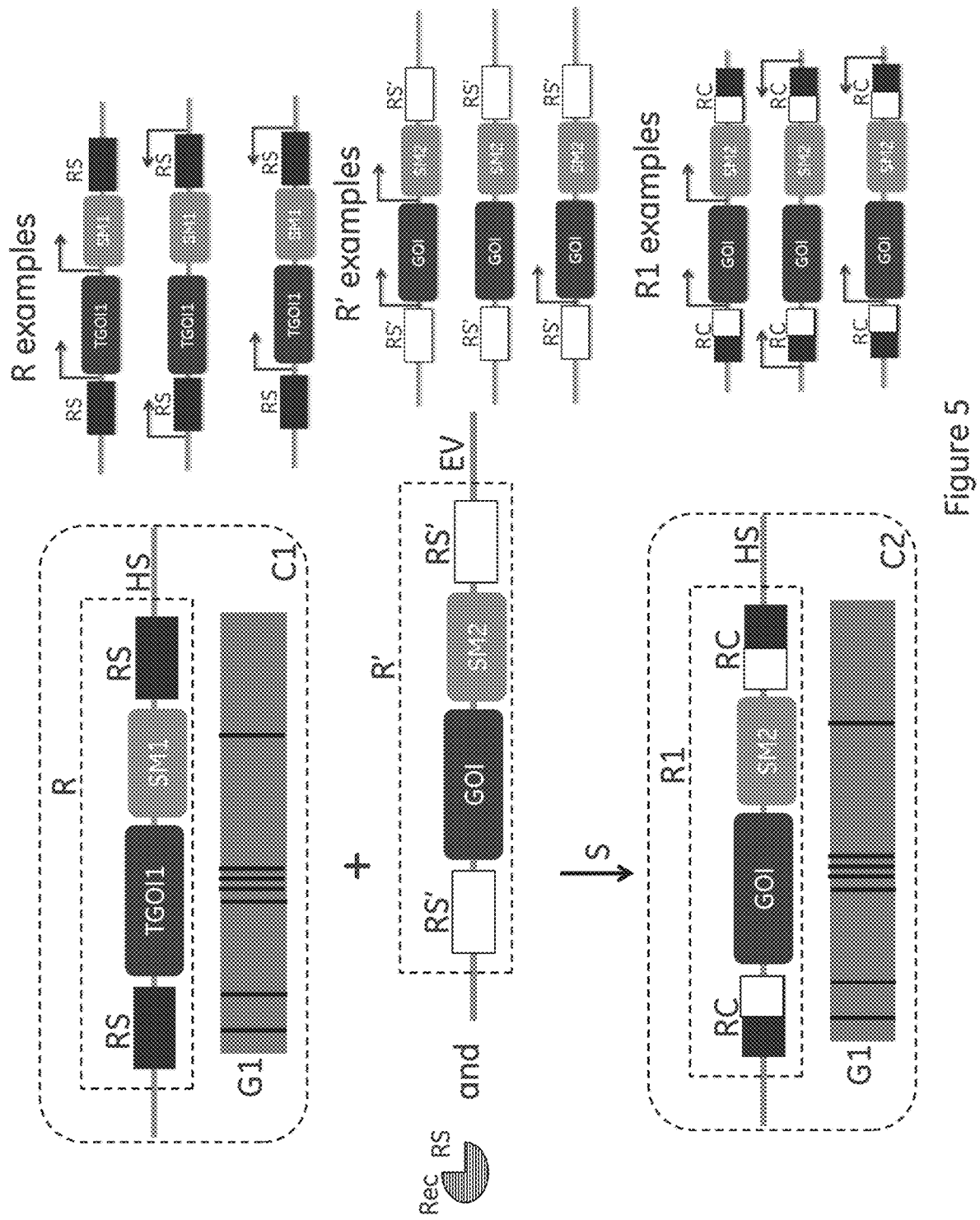
FIG. 5 describes different promoter placement alternatives for a specific embodiment for CLD using an improved cell C1 of the FIG. 1 method using cassette exchange based on dual recombinase recognition sequences RS and a recombinase Rec-RS to exchange a TGOI for a desired GOI.

A second approach utilizes a template DNA construct design R in which a TGOI(s) and a SM gene(s) are flanked by two recombinase recognition sequences (RS) and an expression vector design in which a GOI(s) and a second SM gene(s) are flanked by matching recombinase recognition sequences (RS'). By co-transfecting the improved cell C1 with the expression vector in the form of a plasmid and a plasmid encoding a recombinase (Rec) with specificity for RS/RS' a cassette exchange between R and R' is achieved. A cell C2 having undergone the correct exchange only can be selected via the difference in SMs between R and R'. The resulting recombinant DNA construct R1 contains recombined recombinase recognition sequences RC. Depending on the recombinase system used these can either be different from RS and RS' and differ between the 5' and 3' sequences (as for attP/attB/PhiC31) or be identical to RS/RS' (as for loxP/Cre). The recombinase recognition sequences used can be of any type such as a serine recombinase type such as attP/attB or a tyrosine recombinase type such as Lox, Rox or FRT together with matching recombinases such as PhiC31, Cre, Dre, or Flp. Different examples of this approach based on varying the promoter placement for TGOI/GOI and SMs are outlined in FIG. 5.

Figure 6:
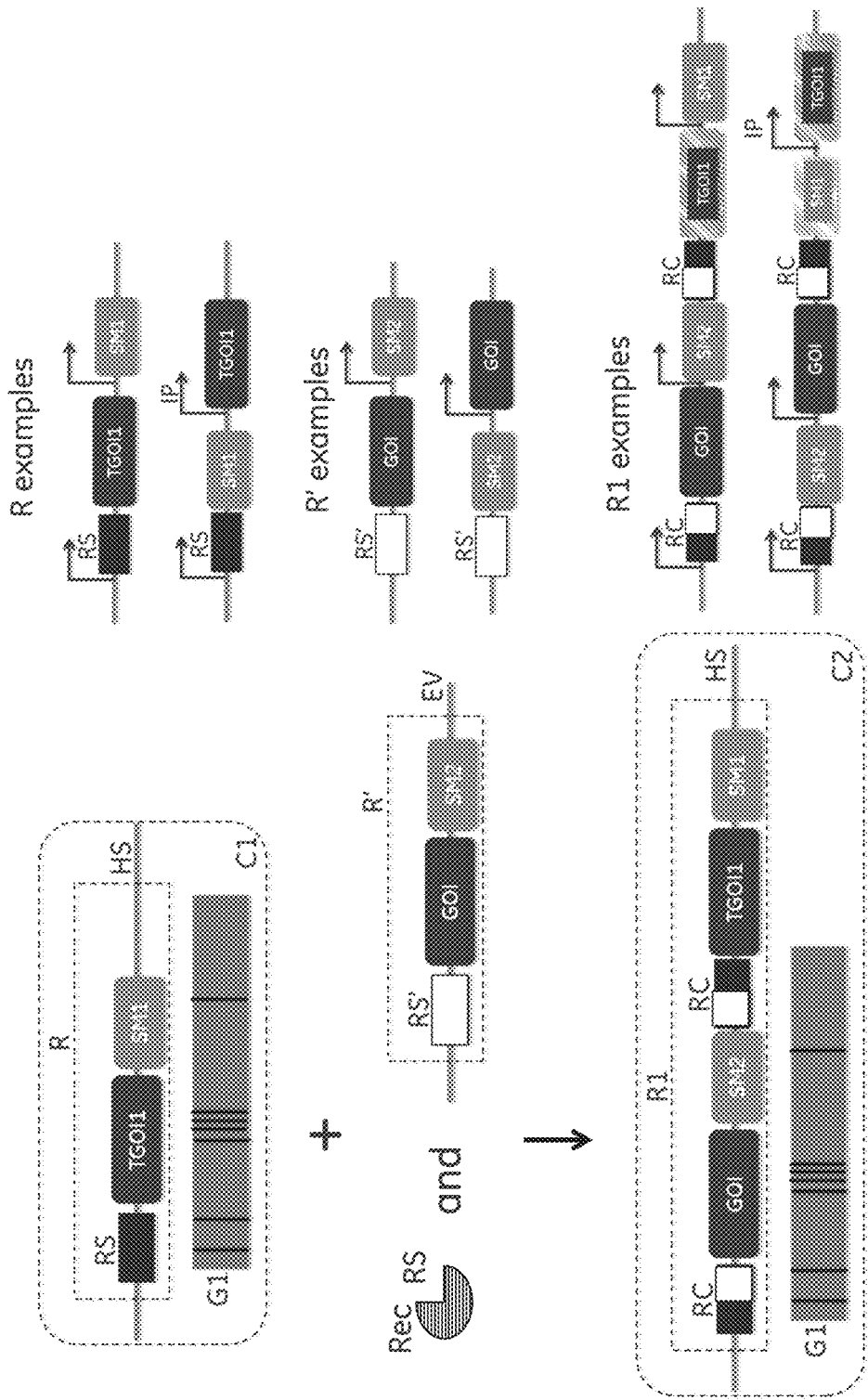
FIG. 6 describes two promoter placement alternatives for a specific embodiment for CLD using an improved cell C1 of the FIG. 1 method based on using a single recombinase recognition sequence RS and a recombinase Rec-RS to introduce a desired GOI with the TGOI remaining but becoming inactivated or possible to inactivate during culture.

In a third approach (FIG. 6) the template DNA construct R contains a single recombinase recognition sequence RS followed by a TGOI(s) and SM gene(s) in any order and the matching expression vector EV a single matching recombinase recognition sequence RS' followed by a GOI(s) and a SM gene(s) in any order. By co-transfecting the improved cell C1 with the expression vector in the form of a plasmid and a plasmid encoding a recombinase (Rec) with specificity for RS/RS' the R' construct is introduced into the cell and simultaneously changing the relative position of the original R construct so that the resulting R1 recombinant DNA construct is a combination of R and R'. In one example the promoter driving TGOI is placed 5' of RS so that TGOI expression is de-activated following R' integration. In another example the promoter driving a SM gene is placed 5' of RS so that the activity of SM1 is deactivated and SM2 is activated upon integration. Further the TGOI in this example is driven by an inducible promoter (IP) so that TGOI expression activity can be shut down following GOI integration by culturing cells in conditions were the inducible promoter is not active but the promoter driving GOI expression is.

In any of the above embodiments of the invention the TGOI/GOI could contain a single gene of interest coding for proteins such as growth factors, blood clotting factors, cytokines, hormones, erythropoietins, albumins, virus proteins, virus protein mimics, bacterial proteins, bacterial protein mimics, domain antibodies, ScFvs, Affibodies, DARPINs, multimerization domains, IgG Fc domains, albumin binding domains, Fc receptor binding domains or fusion proteins based on combinations of the above single gene of interest coded protein classes. The TGOI/GOI could also contain two or more genes of interest coding for proteins such as monoclonal antibodies based on naturally occurring scaffolds, bi-specific antibodies based on naturally occurring scaffolds, Fabs, virus like particles, multiple chain proteins based on association of two or more different protein chains selected from the list of single gene coded proteins above. In preferred embodiments of the invention the TGOI of the host cell line and the GOI used for CLD encode proteins belonging to the same protein class. In further preferred embodiments the TGOI is a hard to express protein of that protein class.

In further preferred embodiments a single copy of TGOI and GOI is used. In further preferred embodiments genetic elements, such as promoter(s), 5'-UTR(s), signal peptide(s), design principle for synonymous nucleotide encoding in the coding region and 3'-UTR(s), used in the TGOI and GOI are identical. In some embodiments multiple final host cell lines containing different TGOIs of the same protein class but with different amino acid ratios are available and the specific cell line used for CLD using a specific GOI is selected based on closest match between amino acid ratios of the template protein of interest (encoded by TGOI) and the desired protein of interest (encoded by GOI). In some embodiments multiple final host cell lines containing identical TGOIs but selected/derived to display a specific protein quality profile, such as a specific glycoprofile, are available. The specific cell line used for CLD using a specific GOI is selected based on closest match between desired protein quality profile and available protein quality profiles.

REFERENCES

[1] Hacker, D. L., De Jesus, M., Wurm, F. M., 2009. 25 years of recombinant proteins from reactor-grown cells—where do we go from here? Biotechnology Advances 27, 1023-1027.
[2] Wirth, D., et al., Road to precision: recombinase-based targeting technology for genome engineering. Current Opinion in Biotechnology, 2007.
[3] D. Wirth, L. Gama-Norton, R. Schucht, K. Nehlsen "Site-Directed Engineering of Defined Chromosomal Sites for Recombinant Protein and Virus Expression— Site-directed engineering of defined chromosomal sites", BioPharm International, Volume 22, Issue 7 (2009)
[4] Alexandra Baer and Jurgen Bode, Coping with kinetic and thermodynamic barriers: RMCE, an efficient strategy for the targeted integration of transgenes, Current Opinion in Biotechnology 2001, 12:473-480
[5] Wei-shou Hu; Cell Culture Bioprocessing Engineering; ISBN 978-0-9856626-0-8, pages 127-146
[6] WO2009/075886 (Translation Enhancer Elements, TEEs)
[7] WO2010/98861 (RESCUE)
[8] http://www.chorus.co.at/projects/genomic-stability-of-the-host-cell-line.html, Dec. 3, 2014
[8] chorus.co.at/projects/genomic-stability-of-the-host-cell-line.html, Dec. 3, 2014 [9] Nazanin Dadehbeigi et al.; Robust and efficient recombinant mAb production using a proprietary CHO host cell with improved characteristics identified through directed evolution, conference poster fujifilmdiosynth.com/pdfs/CCE_XIV_Poster_Fay_Saunders.pdf
[10] Eric Rhodes; Gene editing approaches for viable commercial production; conference presentation Bioprocess summit Boston August 2012
[11] U.S. Pat. No. 6,632,672 (Stanford att-site patent).
[12] A Brown et al.; Synthetic promoters for CHO cell engineering; Biotechnology and Bioengineering vol 111 (8) 1638-1647 (2014).
[13] Angelo DePalma; Cell-Line Optimization: Nature or Nurture? Are Great Cell Lines Born or Made? Both!; GEN Nov. 1, 2015 (Vol. 35, No. 19)

The invention claimed is:
1. A method for creating a mammalian cell bank for cell line development comprising the following steps:
   a) providing a recombinant mammalian cell comprising (i) a genomic region that is transcriptionally active during suspension culture of said recombinant cell in a serum free culture medium, and (ii) a recombinant template DNA construct integrated at said genomic region, said recombinant template DNA construct having a region containing elements needed for expression of a template protein of interest and one or several sequence elements enabling the introduction of a donor DNA construct into said template DNA construct;
   b) generating one or several candidate cells or cell populations descended from the recombinant mammalian cell;
   c) measuring production traits of said generated candidate cells or cell populations and selecting a top candidate cell or cell population having improved characteristics for production of said template protein of interest when compared with production of the template protein of interest by the recombinant mammalian cell;
   d) creating a cell bank for cell line development from said top candidate cell or cell population; and
   e) identifying in the cell bank increases in template protein of interest expression compared to the recombinant mammalian cell following introduction of a modified template DNA construct having been modified to provide increased expression for said template protein of interest by using promoters with increasing strength and/or by using different combinations of translation enhancement elements in the 5'-UTR of genes coding for said template protein of interest.

2. The method according to claim 1, wherein said candidate cells or cell populations are generated according to any of the following procedures:
   (a) isolating clones from a culture of said recombinant cell or cell population or descendants thereof; or
   (b) isolating pools or clones after (i) different culture time in a continuous culture format or (ii) different number of individual cultures starting with inoculation of a first culture using said recombinant cell or cell population or descendants thereof and using a volume from a finished culture to inoculate a next culture or (iii) a combination of (i) and (ii); or
   (c) performing targeted engineering by applying gene editing methods to introduce, remove or modify genetic material in the genome of said recombinant cell or cell population or descendants thereof; or
   (d) any combination of procedure (a) to (c).

3. The method according to claim 1, wherein said template DNA construct contains a region coding for one or several selection markers selected from the group consisting of a fluorescent protein gene; a toxin, an antibiotic resistance gene, and a metabolic enzyme.

4. The method according to claim 3, wherein said recombinant cell or cell population used to generate said candidate cells or cell populations are designed to require an active selection marker for survival and growth of cells.

5. The method according to claim 1, wherein said production traits contain at least one trait selected from the following list; cell growth, cell viability, cell specific productivity for the template protein of interest, template protein of interest aggregate level, glycosylation profile for the template protein of interest, glycosylation site occupancy for the template protein of interest, level of tertiary structure heterogeneity for the template protein of interest, level of recombinant host cell proteins secreted into the culture medium, level of lactate production, level of ammonium production, level of glucose consumption rate, performance in a pre-defined platform bioprocess, and cellular genome stability.

6. The method according to claim 1, wherein a promoter(s) is used for expression of said template protein of interest, and wherein the promotor(s) are mCMV or hCMV, and wherein said region for expression of said template protein of interest by the one or several candidate cells or cell populations has been designed for improved translational efficiency via the presence of translation enhancement elements in the 5'-UTR of said template of interest constructs and/or via nucleotide sequence optimization of the protein coding sequence of said template protein of interest coding gene(s) when compared with the translational efficiency of the recombinant mammalian cell.

7. The method according to claim 1, wherein steps (a) to (e) of claim 1 are iterated in the following way:
 (i) in a next iteration the top candidate cell population from previous step (e) is used as said recombinant mammalian cell in step (a) after having exchanged said template DNA construct for a modified template DNA construct having been modified to provide increased expression for said template protein of interest compared to template DNA constructs in earlier iterations; and
 (ii) repeating (a) to (e) until the top candidate cell or cell population has desired properties, based on the accumulation of one or multiple targeted changes.

8. The method according to claim 1, further comprising exchanging expression of the template protein of interest for expression of the desired protein of interest by using an expression vector to introduce said donor DNA construct into said genomic region of a cell or cell population obtained from said cell bank.

9. The method according to claim 8, wherein the exchange of template DNA construct to said modified template DNA constructs is achieved in the following way:
 (a) each template DNA construct is designed to have conserved sequence stretches in their 5'- and 3'-ends that are homologous to said genomic region;
 (b) each template DNA construct is designed to have a gene editing nuclease target sequence where the sequence differs between generation z and z+1;
 (c) template DNA constructs of generation z and z+1 contain different selection marker(s);
 (d) a template DNA construct of generation z+1 is introduced together with a gene editing expression vector construct into a cell or cell population containing a DNA construct of generation z and wherein the gene editing expression vector codes for a gene editing nuclease with specificity for said target sequence of the template DNA construct of generation z;
 (e) cells having undergone the correct exchange via double strand break catalyzed cellular repair mechanisms are enriched by using the difference in selection markers between DNA constructs of generation z and z+1; and
 (f) DNA analysis methods are applied to ensure the correct exchange for the cells.

10. The method according to claim 1, wherein said mammalian host cell line is a CHO cell line selected from CHO DG44, CHO K1, CHO M, CHO-S and a CHO GS knockout cell line.

11. The method of according to claim 1, wherein the donor DNA construct comprises a region encoding a desired protein of interest belonging to the same class as the template protein of interest and the desired protein of interest and template protein of interest are selected from: i) a protein encoded by two or more genes of interest selected from monoclonal antibodies based on naturally occurring scaffolds, bi-specific antibodies based on naturally occurring scaffolds, Fabs, and virus like particles, and ii) a protein encoded by a single gene of interest, selected from growth factors, blood clotting factors, cytokines, hormones, erythropoietins, albumins, virus proteins, virus protein mimics, bacterial proteins, bacterial protein mimics, domain antibodies, ScFvs, Affibodies, DARPINs, multimerization domains, IgG Fc domains, albumin binding domains, and Fc receptor binding domains and fusion proteins based on combinations of the single gene of interest.

* * * * *